Figure 1:
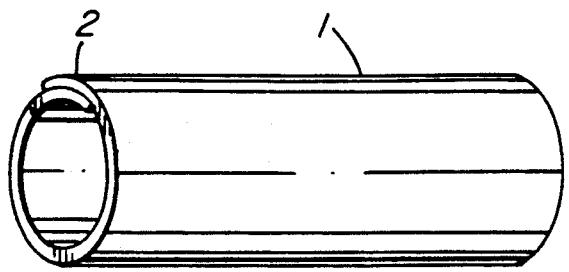

United States Patent [19]

Stiles

[11] Patent Number: 5,089,006

[45] Date of Patent: Feb. 18, 1992

[54] BIOLOGICAL DUCT LINER AND INSTALLATION CATHETER

[76] Inventor: Frank B. Stiles, P.O. Box 25, Northport, Nova Scotia, Canada, B0L 1E0

[21] Appl. No.: 443,002

[22] Filed: Nov. 29, 1989

[51] Int. Cl.⁵ .............................................. A61M 29/00
[52] U.S. Cl. ........................................ 606/198; 623/1; 623/12
[58] Field of Search ............... 606/194, 195, 191, 198; 623/1, 12; 604/8, 104

[56] References Cited

U.S. PATENT DOCUMENTS

| | | | |
|---|---|---|---|
| 4,665,918 | 5/1987 | Garza et al. | 623/12 |
| 4,733,665 | 3/1988 | Pazmaz | 623/1 |
| 4,739,762 | 4/1988 | Pazmaz | 623/1 |
| 4,740,207 | 4/1988 | Kreamer | 623/1 |
| 4,856,516 | 8/1989 | Hillstead | 623/1 |
| 4,877,030 | 10/1989 | Beck et al. | 623/1 |
| 4,878,906 | 11/1989 | Lindemann et al. | 623/1 |
| 4,922,905 | 5/1990 | Strecker | 606/195 |
| 4,923,464 | 5/1990 | DiPisa, Jr. | 606/195 |

Primary Examiner—C. Fred Rosenbaum
Assistant Examiner—William W. Lewis
Attorney, Agent, or Firm—Pascal & Associates

[57] ABSTRACT

An apparatus for correcting narrowing of a fluid vessel of the body comprising a catheter, for insertion into the blood vessel at a location remote from a region of narrowing, and a fluid vessel liner. The liner is comprised of a radially resiliently compressible tube having an elongated split along one side thereof. The edges of the sides of the liner on each side of the split overlap each other. The liner is contained within the catheter adjacent a tip of the catheter in a compressed condition. The catheter is constructed for expulsion of the liner from the catheter forward of the catheter at the region of narrowing, thereby facilitating expansion of the tube to a natural expanded condition so as to support the blood vessel from the interior to the diameter of the tube in its naturally expanded diameter.

7 Claims, 3 Drawing Sheets

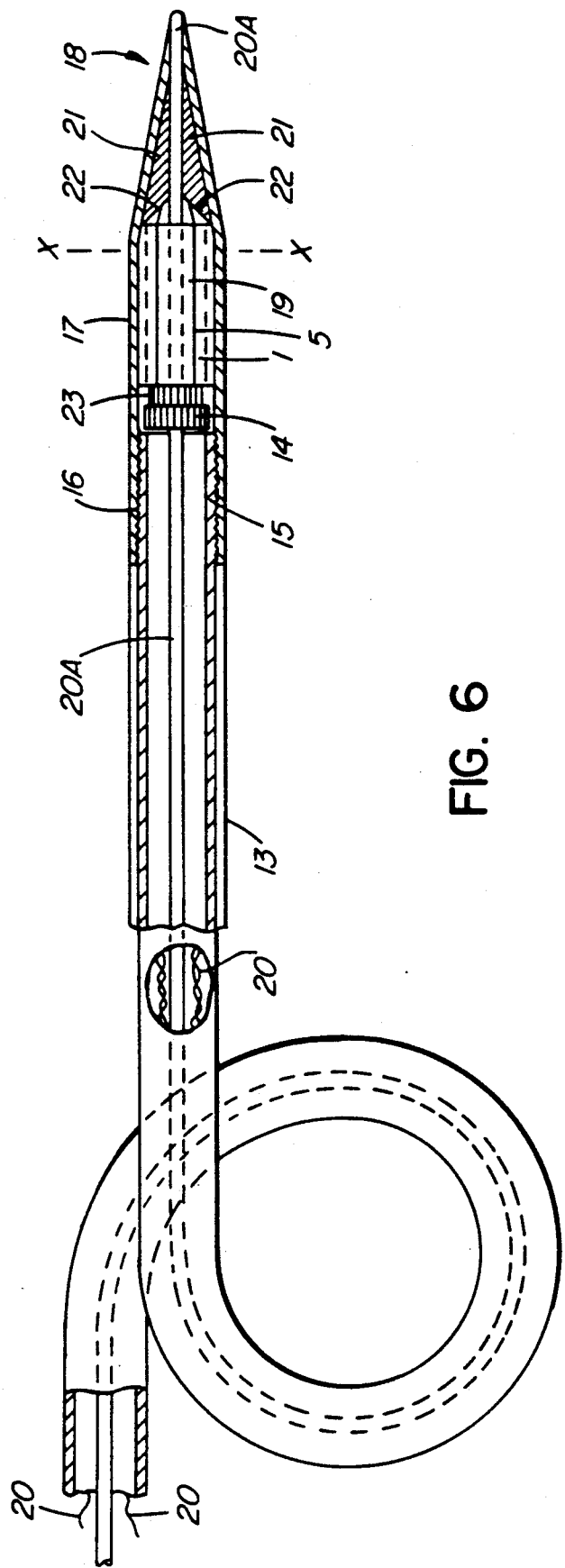
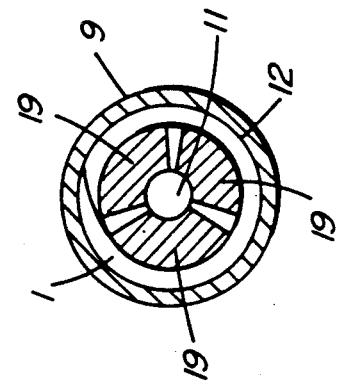
FIG. 6
FIG. 7

BIOLOGICAL DUCT LINER AND INSTALLATION CATHETER

This invention relates to a catheter, and in particular to a catheter for installing a liner or sleeve device in an artery or other biological duct in order to maintain it permanently or temporarily in a dilated state.

One of the techniques used for clearing blocked arteries, for example, arteries clogged by cholesterol, is to insert a catheter to the site of the blockage. The end of the catheter is then expanded, e.g. by expansion of a balloon at the site of the blockage. This expansion compresses the cholesterol, allowing the passage of blood. However this technique has not always worked, and in addition, another build-up often occurs at the same site which again blocks the artery.

In order to ensure that the artery is maintained in an expanded state, Dominic M. Wiktor, in U.S. Pat. No. 4,649,922 issued Mar. 17th, 1987, describes a catheter which contains a balloon for compressing cholesterol, the catheter being structured so that a liner formed of stainless steel spring is deployed at the site of the blockage, and is maintained in place after the catheter has been removed. However this structure, using a helical spring, has a diameter that must be narrower than the artery itself in order to be inserted. Yet due to the structural form of the catheter the spring, is wider in diameter before deployment than after deployment, and in its widest diameter state is significantly narrower than the artery itself. It cannot expand to an optimal diameter in order to maintain the interior of the artery to an optimal diameter.

The present invention is a biological vessel sleeve which is inserted in place while maintaining a diameter which is narrower than the duct, but expands to an optimal diameter which is significantly greater than its diameter during insertion.

In addition, the sleeve is coated by a material which rejects adhesion by blood or cholesterol, the coating being preferably Teflon TM.

One embodiment of the invention is a fluid vessel liner comprised of a compressible tube having an elongated split along one side thereon, the sides of the tube on each side of the split overlapping each other.

Another embodiment of the invention is an apparatus for correcting narrowing of a fluid vessel of the body comprising a catheter, for insertion into the blood vessel at a location remote from a region of narrowing, a fluid vessel liner comprised of a radially resiliently compressible tube having an elongated split along one side thereof and the edges of the sides of the liner on each side or the split overlapping each other contained within the catheter adjacent a tip of the catheter in a compressed condition, apparatus for expulsion of the liner from the catheter forward of the catheter at the region of narrowing, and apparatus for facilitating expansion of the tube to a natural expanded condition thereby to support the blood vessel from the interior to the diameter of the tube in its naturally expanded diameter.

In a further embodiment of the invention the tube is formed of magnetically attractable metal. The apparatus for facilitating expansion is comprised of an electromagnet for containment within the tube, and for attracting and radially compressing the compressible tube thereto by means of a controllable electromagnetic field when the tube is contained within the catheter, and for releasing the compressible tube by liquidating the electromagnetic field when the compressible tube is in a deployment position at the region of narrowing, thus allowing the compressible tube to expand to a predetermined diameter.

While the description herein may appear to be mainly directed to application to blood vessels, the invention is not intended to be so limited. The invention is equally applicable to all biological ducts, including urological ducts.

Figure 3:
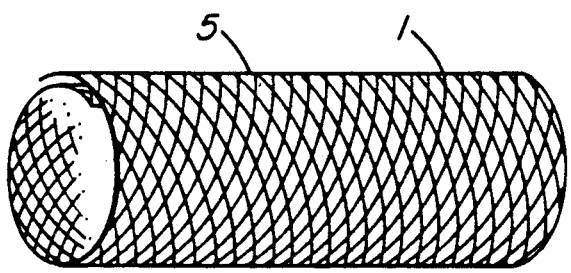
Figure 4:
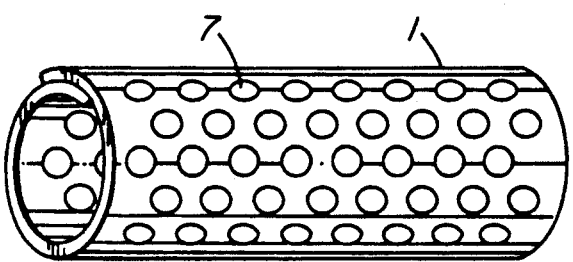
Figure 5:
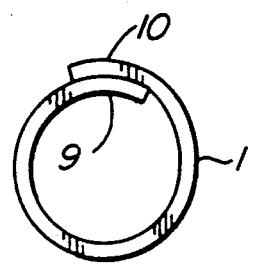
Figure 8:
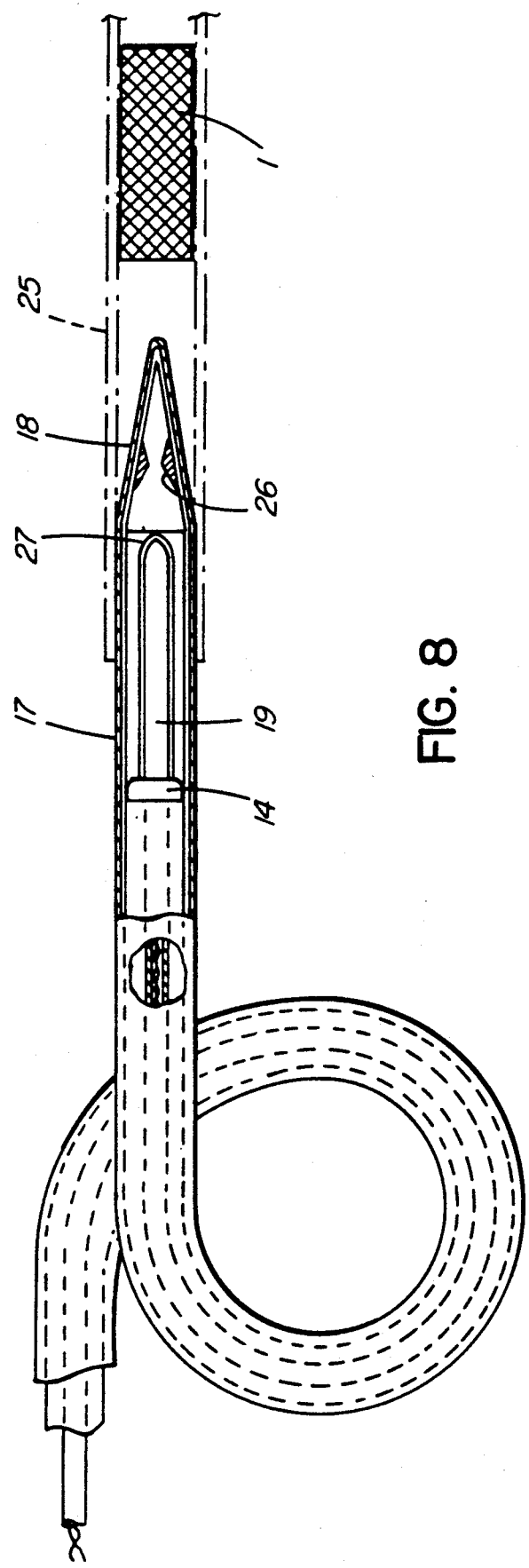
Figure 9:
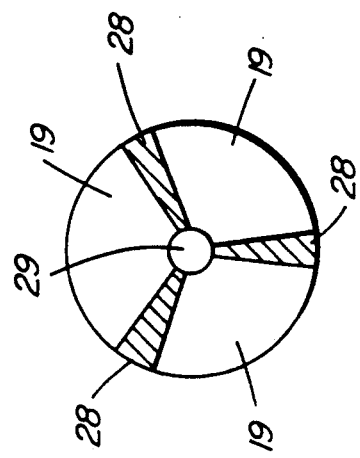

A better understanding of the invention will be obtained upon reading the description below, in conjunction with the following drawings, in which:

FIGS. 1–4 are isometric views of various types of biological sleeves, as contemplated by the present invention, FIG. 5 is an end view of a biological sleeve as contemplated in the present invention, FIG. 6 is a partly sectional view of the end of a catheter containing the biological sleeve, prior to deployment, FIG. 7 is a cross-sectional view along section X—X of FIG. 6, FIG. 8 is a partly sectional view of a catheter in accordance with the present invention of a type designed to retrieve an already deployed sleeve, and FIG. 9 is a cross-section along section Y—Y of FIG. 8.

Turning now to FIGS. 1–5, a sleeve 1 formed of a cylinder of spring sheet stainless steel coated with Teflon TM (polytetrafluoroethylene) is shown. The cylinder is axially slit, the edges along the slit overlapping as shown at 2. It may be seen that the sleeve can be radially compressed, and will spring back to a predetermined diameter, due to the spring nature of the stainless steel. An outer side of the sleeve 10 can slip past an inner side of the sleeve 9, during compression. In the embodiment shown in FIG. 1, the surfaces of the sleeve are smooth and are not generally perforated.

Figure 2:
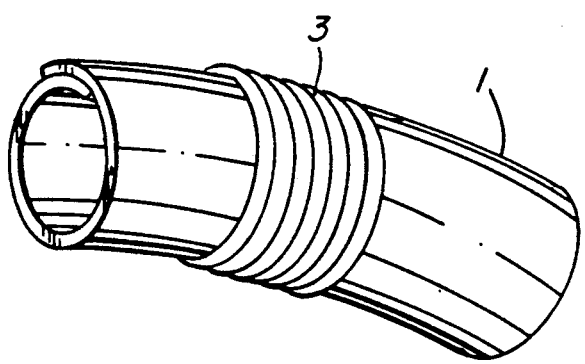

The embodiment shown in FIG. 2 contains circular corrugations 3. This allows the sleeve to be bent permanently. Prior to deployment, however, the sleeve is straightened against the spring tendency to maintain it in the bent position. It will be temporarily maintained in its straightened position within the deployment catheter to be described below.

The embodiment shown in FIG. 3 is formed of stainless steel mesh 5, which can be used in a biological duct in which the maximum interior surface area of the duct must be exposed. The embodiment of FIG. 4 is formed of stainless steel spring sheet which has been punched with a large number of holes 7. This structure provides more strength than the structure of FIG. 3, but allows significant areas of the inner surface of the biological duct to be exposed to fluids passing therethrough. The embodiments of FIGS. 3 and 4 can of course contain circular corrugations as in FIG. 2, in order that the sleeve can be permanently bent.

It should be noted that it is possible the sleeves as shown in FIGS. 3 and 4 will "grow into" (be incorporated into) the wall of the biological duct after some time, and will become an integral part of the duct. This can be better accomplished by not coating the outside of the sleeves with Teflon TM.

FIG. 6 illustrates a sleeve deployment catheter. A catheter sleeve 13 contains a plunger head 14, contained at the end of a plunger rod 15. The plunger rod can slide within the catheter sleeve 13 either by being coupled by a thread 16, the plunger rod rotating within the catheter sleeve, or, if no thread is used, by simple manual sliding manipulation.

A nose cone 17 at the front of the sleeve over the plunger head terminates in a conical tip 18.

With additional reference to FIG. 7, a sleeve 1 of a type described with reference to FIGS. 1–5 is contained within the nose cone 17, behind the conical tip, in its compressed state. The sleeve is maintained in the compressed state by means of electromagnets 19, which are symmetrically disposed around the axis of the instrument within the sleeve and are fixed to the front of the plunger head 14. The electromagnets can extend over the length of the sleeve, or shorter magnets can be used if sufficient total magnetic strength is used to maintain the sleeve in its compressed condition. Wires 20, used to power the electromagnetics, extend through the plunger head 14 and through the catheter, and are coupled to a power supply outside the body of the patient, via a switch (not shown).

The conical tip is formed of an inert material 21, and contains at its end adjacent the sleeve 1 and electromagnets 19, a conical chamfer 22. The end 23 of the plunger head 14 has a diameter of the inner diameter of the nose cone 17 so that it bears against the edge of sleeve 1, which bears against the chamfer 22. A tube 20A extends the length of the catheter.

In operation, the catheter containing the sleeve which is compressed under the influence of the magnetic field of magnets 19 is inserted into the biological duct to be expanded. When near the site to be expanded, dye is inserted into the outer end of tube 20A, and passes down the tube 20A to pass out of the conical tip 18 into the biological duct, so that the restricted area to be expanded can be viewed by X-ray, and thus to ensure that the sleeve is pushed to the correct location.

With the conical tip located just behind the region of the biological duct to be expanded, the plunger rod is moved forward, either by rotating it, and thus thrusting it forward by mutual action of the threading 16, or if threading is not used, by manual movement of the plunger rod within the catheter sleeve 13.

This causes the plunger head 14 to push the plunger end 23 against the sleeve 1 The sleeve 1 and magnets 19, are forced against the inner portion of the conical tip 18. Due to force against the conical chamfer 22, the conical tip 18, which is split in its length at, for example, three locations 120° apart, and causes the conical tip 18 to open, hinged at the ends of the chamfer by the resilient plastic material of the conical tip. The sleeve 1, maintained in its compressed position by the electromagnetic field of the electromagnets 19, is pushed out of the catheter, forward of conical tip 18, with its outer surface finally adjacent the inner surface of the biological duct at the location where the biological duct is to be expanded.

The electric current to the electromagnets is then turned off, by opening of the external switch described earlier. With the electromagnetic field thus switched off, the force maintaining the sleeve compressed is removed, and the sleeve expands to its predetermined diameter, under spring tension. The plunger 14 is withdrawn back into the nose cone 17, with the electromagnets fixed to the conical head 23 following. The conical chamfer 22, bearing on the electromagnets allow the jaws of the nose cone to resiliently close toward each other following passage of the electromagnets 19 into the nose cone, allowing the conical tip 18 to close. The jaws of conical tip 18 can be an inert resilient plastics material coupled via integral plastics spring to the remainder of nose cone 17, in a well known manner.

With the electromagnets 19 safely contained within the catheter, and the nose cone 18 closed, the catheter is withdrawn. The sleeve 1, being expanded, both compresses any cholesterol that may be present along the duct wall, and expands the interior of the biological duct, maintaining it in its expanded condition.

In the event the sleeve is to be placed in a biological duct at the location of a bend, the sleeve shown in FIG. 2 is used. While it is permanently bent so as to maintain the bent condition under spring loaded tension as described above once deployed, it is resiliently bent into a straight cylindrical form against the spring tension prior to being inserted into the catheter. After deployment and release of the electromagnetic field, the sleeve can assume its permanently bent orientation.

FIGS. 8 and 9 illustrate a catheter for retrieving a sleeve already in position. Illustrated in FIG. 8 is a biological duct 25 containing a sleeve 1 that has been previously deployed. While a form of the catheter shown in FIG. 6 could be used for retrieval, a modified form of it is preferred to be used as the retrieving catheter, as shown in FIG. 8.

The catheter is inserted into the biological duct, and to a position just adjacent the front of sleeve 1. A plunger head 14 has attached to the front thereof a set of electromagnets 19 as described earlier. In this embodiment, however, a dye tube is not necessary. In addition, the interior of nose cone 17 contains inwardly directed sloping edges 26 to form cam surfaces. The forward end 27 of electromagnets 19 can be smoothly conical in shape.

In operation, the plunger head 14 is moved forward, pushing the electromagnets 19 forward. The forward end of the electromagnets come into contact with the sloping edges 26 of the interior of the nose cone 17, forcing the jaws of the nose cone open. The electromagnets are pushed forward into the interior of the sleeve 1. Due to the opacity of the sleeve 1 and the catheter, the positioning can be seen clearly by X-ray. However in case dye is to be injected, the structure can contain an interior tube 20A as described earlier with respect to FIG. 6.

Once the electromagnets 19 are in position, with the end of the plunger head against the adjacent end of sleeve 1, the external switch is closed and electric current is applied to the electromagnets 19. The sleeve 1 is attracted to the electromagnet, and compresses by the outer side of the sleeve 10 sliding over the inner side of the sleeve 9 (FIG. 5). The sleeve 1 thus is wrapped around the electromagnets 19 in a compressed state, and is magnetically adhered thereto.

The plunger rod is then withdrawn, drawing the plunger head, electromagnets and sleeve into the nose cone 17. As the outer edge of sleeve 1 and the forward end 27 of the electromagnets pass the sloping edges 26 of the interior of the conical tip 18, the jaws of the conical tip close. The sleeve is thus safely contained within the catheter. The catheter is then withdrawn from the biological duct with the sleeve.

It is preferred that three identical electromagnets 19 symmetrically located about the axis of the catheter should be used, preferably insulated from each other by means of inert resilient insulation 28. The wires 20 can pass through the insulation 28 parallel to the axis of the catheter in order to connect to electromagnetic field generating coils forming part of the electromagnets 19. In addition, a center core 29 of the electromagnets can be filled with inert resilient material, such as silicone rubber, and may contain the wires.

It should be noted that the catheter sleeve can be used to insert an ultrasonic transducer, such as a miniature quartz crystal, into the biological duct, in place of the conical tip. Wires for operating the transducer can be passed through the catheter to imaging electronics outside the body. The head can be used for imaging the interior of the duct, and surrounding structures.

A person skilled in the art understanding the present invention may now conceive of variations or other embodiments using the concepts described herein, such as other means for compressing the sleeve. All are considered to be within the sphere and scope of the invention as defined in the claims appended hereto.

I claim:

1. A biological fluid vessel liner forming a sleeve comprised of a radially compressible tube having an elongated split along one side thereof, the sides of the tube on each side of the split overlapping each other, a tube being covered on all surfaces with polytetrafluoroethylene, the cross-section of the tube being circular, the tube containing annular corrugations therein over a predetermined length, for providing a region allowing the tube to be permanently bent away from a linear axis.

2. Apparatus for correcting narrowing of a fluid vessel of a biological body comprising a catheter, for insertion into the blood vessel at a location remote from a region of narrowing, a fluid vessel liner comprised of a radially resiliently compressible tube having an elongated split along one side thereof and the edges of the sides of the liner on each side of the split overlapping each other contained within the catheter adjacent a tip of the catheter in a compressed condition, means for expulsion of the liner from the catheter forward of the catheter at the region of narrowing, and means for facilitating expansion of the tube to a natural expanded condition thereby to support the blood vessel from the interior to the diameter of the tube in its naturally expanded diameter, in which the tube is formed of magnetically attractable metal, and in which the means for facilitating expansion is comprised of an electromagnet for containment within the tube, and for attracting and radially compressing the compressible tube thereto by means of a controllable electromagnetic field when the tube is contained within the catheter, and for releasing the compressible tube by liquidating the electromagnetic field when the compressible tube is in a deployment position at the region of narrowing, thus allowing the compressible tube to expand to a predetermined diameter.

3. Apparatus as defined in claim 2, the catheter further comprising an axially split nose cone having a plurality of jaws resiliently biased to a closed position, located immediately ahead of the compressible tube when contained within the catheter, the interior of the nose cone containing a conical chamfer immediately adjacent the compressible tube, whereby when the compressible tube is pushed forward to facilitate expulsion, the compressible tube rides against the conical chamfer, forcing open the jaws of the nose cone.

4. Apparatus as defined in claim 3, further including an axial tube extending substantially the length of the catheter, for carrying dye to the front of the nose cone.

5. Apparatus as defined in claim 2, in which the electromagnet is formed of three similar segments located 120° apart symmetrically about the axis of the catheter, separated by a resilient insulator means, wires for the electromagnet segments passing along or parallel to the axis of the catheter to the exterior of the catheter for connection to control apparatus.

6. A method for expansion of a biological fluid vessel, comprising radially contracting a radially resiliently compressible liner, inserting the liner to a position in said vessel, and allowing the liner to expand to a predetermined diameter, in which the liner is formed of a longitudinally split tube of magnetic material having overlapping edges along the split, the contracting step being comprised of applying a magnetic field to the material to cause radial contraction and overlap of the overlapping edges additional to the overlap achieved in the absence of said field.

7. A method as defined in claim 6, in which the step of applying a magnetic field is comprised of inserting an electromagnet axially within the liner, and applying electric current to the electromagnet.

* * * * *